United States Patent [19]
Scheinberg et al.

[11] Patent Number: 6,156,316
[45] Date of Patent: *Dec. 5, 2000

[54] ONCOGENE FUSION PROTEIN PEPTIDE VACCINES

[75] Inventors: David A. Scheinberg, New York, N.Y.; Alessandro Sette, La Jolla, Calif.; Monica Bocchia, New York, N.Y.

[73] Assignees: Sloan-Kettering Institute for Cancer Research, New York, N.Y.; Cytel Corporation, San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/437,175

[22] Filed: May 8, 1995

[51] Int. Cl.[7] .............................. A61K 39/00; C07K 7/00
[52] U.S. Cl. ...................... 424/185.1; 424/192.1; 424/277.1; 435/7.1; 435/7.24; 435/325; 435/366; 514/2; 514/12; 514/13; 514/14; 514/15; 530/324; 530/325; 530/326; 530/327; 530/328
[58] Field of Search ........................... 435/7.1, 7.24; 514/2, 12–15; 530/324, 328; 424/184.1, 185.1, 192.1, 277.1

[56] References Cited

U.S. PATENT DOCUMENTS 5,320,947  6/1994  Cheever et al. .
5,961,978  10/1999  Gaudernack et al. .

FOREIGN PATENT DOCUMENTS 9420127  9/1994  WIPO .

OTHER PUBLICATIONS

Chen, et al., *Proc. Natl. Acad. Sci. USA* (1992) 89:1468–1472.

Cullis, et al., *Leukemia* (1994) 8:165–170.

Cellis, et al., *Proc. Natl. Acad. Sci. USA* (1994) 91:2105–2109.

Gambacorti–Passerini, et al., *Blood* (1994) 84(Supp. 1):618a, abstract no. 2459.

Drexler, et al., *Leukemia* (1995) 9:480–500.

Bocchia, et al., *Blood* (May 15, 1995) 85:2680–2684.

*Primary Examiner*—Marianne P. Allen
*Attorney, Agent, or Firm*—John P. White; Cooper & Dunham LLP

[57] ABSTRACT

Fusion-point spanning peptides, for example BCR-ABL fusion breakpoint peptides associated with chronic myelogenous leukemia (CML), bind major histompatibility complex molecules, such as HLA class I molecules, and induce cytotoxic T cell proliferation. The breakpoint peptides can be used as vaccines.

8 Claims, 3 Drawing Sheets

FIGURE 1A b3a2, 21 amino acid sequence

| H | S | A | T | G | F | K | Q | S | S | K | A | L | Q | R | P | V | A | S | D | F |

| H | S | A | T | G | F | K | Q | S | S | K |
| S | A | T | G | F | K | Q | S | S | K | A |
| A | T | G | F | K | Q | S | S | K | A | L |
| T | G | F | K | Q | S | S | K | A | L | Q |
| G | F | K | Q | S | S | K | A | L | Q | R |
| F | K | Q | S | S | K | A | L | Q | R | P |
| K | Q | S | S | K | A | L | Q | R | P | V |
| Q | S | S | K | A | L | Q | R | P | V | A |
| S | S | K | A | L | Q | R | P | V | A | S |
| S | K | A | L | Q | R | P | V | A | S | D |
| K | A | L | Q | R | P | V | A | S | D | F |

FIGURE 1B b2a2, 21 amino acid sequence

| H | S | I | P | L | T | I | N | K | E | E | A | L | Q | R | P | V | A | S | D | F |

FIGURE 1C

PML-RAαA, 21 amino acid sequence

| N | H | V | A | S | G | A | G | E | A | A | I | E | T | Q | S | S | S | S | E | E |

FIGURE 1D

PML-RAαB, 21 amino acid sequence

| D | L | S | S | C | I | T | Q | G | K | A | I | E | T | Q | S | S | S | S | E | E |

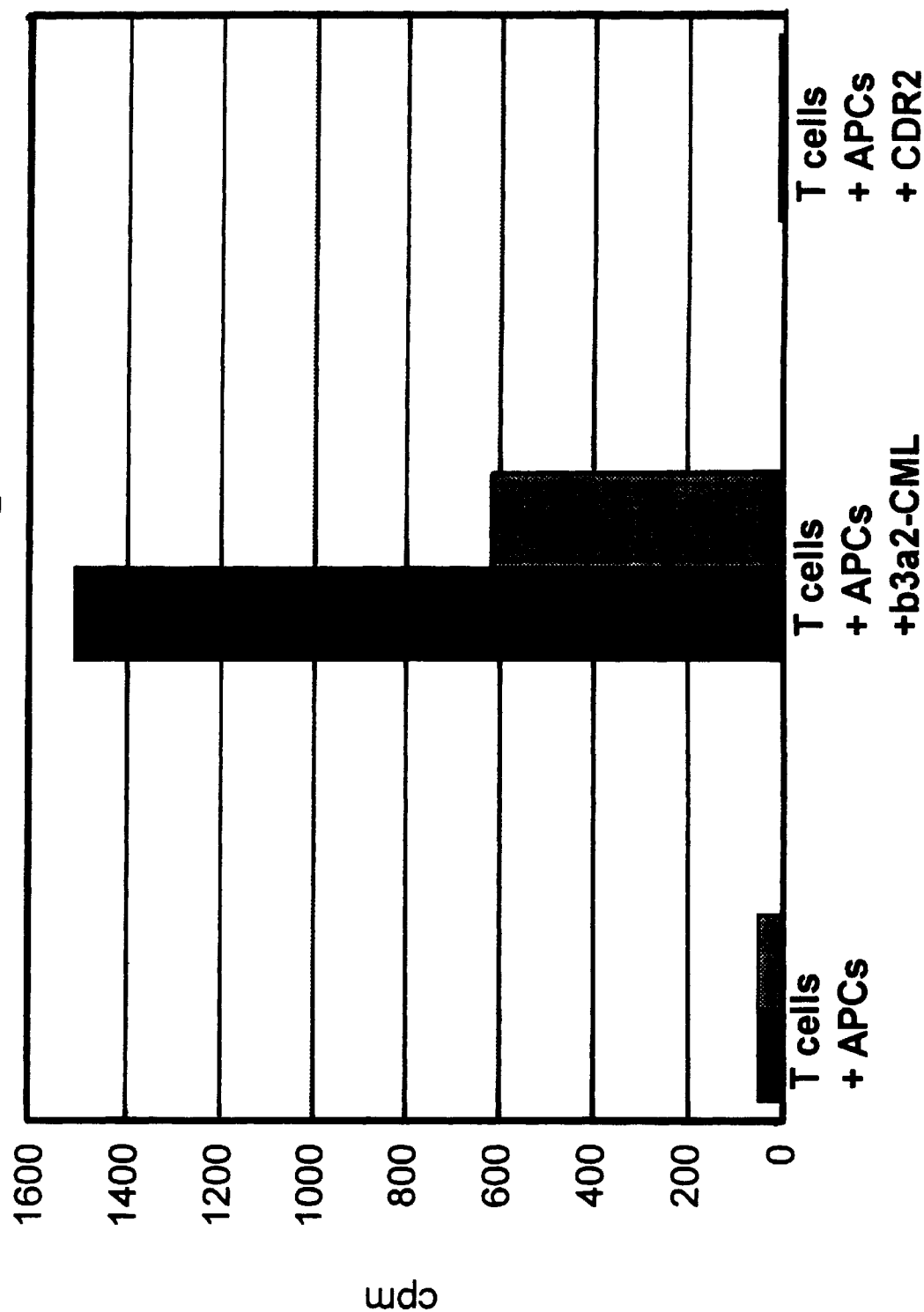

SEQUENCE LISTING (1) GENERAL INFORMATION:

(iii) NUMBER OF SEQUENCES: 36, numbered 1-15 and 17-37

(2) INFORMATION FOR SEQ ID NO:1:

(i) SEQUENCE CHARACTERISTICS:
      (A) LENGTH: 21 amino acids
      (B) TYPE: amino acid

```
        (C) STRANDEDNESS:
        (D) TOPOLOGY: linear (ii) MOLECULE TYPE: peptide (xi) SEQUENCE DESCRIPTION: SEQ ID NO:1:

His Ser Ala Thr Gly Phe Lys Gln Ser Ser Lys Ala Leu Gln Arg Pro
1               5                   10                  15

Val Ala Ser Asp Phe
            20

(2) INFORMATION FOR SEQ ID NO:2:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

His Ser Ala Thr Gly Phe Lys Gln Ser Ser Lys
1               5                   10

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Ser Ala Thr Gly Phe Lys Gln Ser Ser Lys Ala
1               5                   10

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Ala Thr Gly Phe Lys Gln Ser Ser Lys Ala Leu
1               5                   10

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Thr Gly Phe Lys Gln Ser Ser Lys Ala Leu Gln
1               5                   10
```

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Gly Phe Lys Gln Ser Ser Lys Ala Leu Gln Arg
1               5                   10
```

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Phe Lys Gln Ser Ser Lys Ala Leu Gln Arg Pro
1               5                   10
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Lys Gln Ser Ser Lys Ala Leu Gln Arg Pro Val
1               5                   10
```

(2) INFORMATION FOR SEQ ID NO:9:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Gln Ser Ser Lys Ala Leu Gln Arg Pro Val Ala
1               5                   10
```

(2) INFORMATION FOR SEQ ID NO:10:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Ser Ser Lys Ala Leu Gln Arg Pro Val Ala Ser
1               5                   10
```

```
(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Ser Lys Ala Leu Gln Arg Pro Val Ala Ser Asp
 1               5                  10

(2) INFORMATION FOR SEQ ID NO:12:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Lys Ala Leu Gln Arg Pro Val Ala Ser Asp Phe
 1               5                  10

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

His Ser Ile Pro Leu Thr Ile Asn Lys Glu Glu Ala Leu Gln Arg Pro
 1               5                  10                  15

Val Ala Ser Asp Phe
            20

(2) INFORMATION FOR SEQ ID NO:14:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Asn His Val Ala Ser Gly Ala Gly Glu Ala Ala Ile Glu Thr Gln Ser
 1               5                  10                  15

Ser Ser Ser Glu Glu
            20

(2) INFORMATION FOR SEQ ID NO:15:

(i) SEQUENCE CHARACTERISTICS:
        (A) LENGTH: 21 amino acids
        (B) TYPE: amino acid
        (C) STRANDEDNESS:
        (D) TOPOLOGY: linear
```

(ii) MOLECULE TYPE: peptide (xi) SEQUENCE DESCRIPTION: SEQ ID NO:15:

Asp Leu Ser Ser Cys Ile Thr Gln Gly Lys Ala Ile Glu Thr Gln Ser
1               5                  10                  15

Ser Ser Ser Glu Glu
            20

(2) INFORMATION FOR SEQ ID NO:17:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:17:

Ile Pro Leu Thr Ile Asn Lys Glu Glu Ala Leu
1               5                  10

(2) INFORMATION FOR SEQ ID NO:18:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:18:

Pro Leu Thr Ile Asn Lys Glu Glu Ala
1               5

(2) INFORMATION FOR SEQ ID NO:19:

(i) SEQUENCE CHARACTERISTICS:
         (A) LENGTH: 10 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:19:

Pro Leu Thr Ile Asn Lys Glu Glu Ala Leu
1               5                  10

(2) INFORMATION FOR SEQ ID NO:20:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:20:

Leu Thr Ile Asn Lys Glu Glu Ala Leu
1               5

(2) INFORMATION FOR SEQ ID NO:21:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

```
Leu Thr Ile Asn Lys Glu Glu Ala Leu Gln Arg
1               5                  10
```

(2) INFORMATION FOR SEQ ID NO:22:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

```
Thr Ile Asn Lys Glu Glu Ala Leu
1               5
```

(2) INFORMATION FOR SEQ ID NO:23:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

```
Thr Ile Asn Lys Glu Glu Ala Leu Gln Arg
1               5                  10
```

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

```
Ile Asn Lys Glu Glu Ala Leu Gln Arg
1               5
```

(2) INFORMATION FOR SEQ ID NO:25:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

```
Asn Lys Glu Glu Ala Leu Gln Arg
1               5
```

(2) INFORMATION FOR SEQ ID NO:26:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

```
Glu Ala Leu Gln Arg Pro Val Ala Ser Asp Phe
1               5                   10
```

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

```
Ser Ala Thr Gly Phe Lys Gln Ser Ser Lys
1               5                   10
```

(2) INFORMATION FOR SEQ ID NO:28:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

```
Ala Thr Gly Phe Lys Gln Ser Ser Lys
1               5
```

(2) INFORMATION FOR SEQ ID NO:29:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

```
Thr Gly Phe Lys Gln Ser Ser Lys
1               5
```

(2) INFORMATION FOR SEQ ID NO:30:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Gly Phe Lys Gln Ser Ser Lys Ala Leu
1               5
```

(2) INFORMATION FOR SEQ ID NO:31:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
Phe Lys Gln Ser Ser Lys Ala Leu Gln Arg
1               5                   10
```

(2) INFORMATION FOR SEQ ID NO:32:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Lys Gln Ser Ser Lys Ala Leu Gln Arg
1               5
```

(2) INFORMATION FOR SEQ ID NO:33:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
Gln Ser Ser Lys Ala Leu Gln Arg
1               5
```

(2) INFORMATION FOR SEQ ID NO:34:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

```
His Val Ala Ser Gly Ala Gly Glu Ala Ala Ile
1               5                   10
```

(2) INFORMATION FOR SEQ ID NO:35:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
Val Ala Ser Gly Ala Gly Glu Ala Ala Ile
1               5                   10

(2) INFORMATION FOR SEQ ID NO:36:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

Asp Leu Ser Ser Cys Ile Thr Gln Gly Lys Ala
1               5                   10

(2) INFORMATION FOR SEQ ID NO:37:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

Cys Ile Thr Gln Gly Lys Ala Ile
1               5
```

ONCOGENE FUSION PROTEIN PEPTIDE VACCINES

The invention disclosed herein was made with Government support under NIH Grant Nos. R01CA55349 and PO1CA64593 from the Department of Health and Human Services. Accordingly, the U.S. Government has certain rights in this invention.

Throughout this application, various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

The following standard abbreviations are used throughout to refer to amino acids and amino acid residues:

| A | Ala | Alanine       | M | Met | Methionine |
|---|-----|---------------|---|-----|------------|
| C | Cys | Cysteine      | N | Asn | Asparagine |
| D | Asp | Aspartic acid | P | Pro | Proline    |
| E | Glu | Glutamic acid | Q | Gln | Glutamine  |
| F | Phe | Phenylanine   | R | Arg | Arginine   |
| G | Gly | Glycine       | S | Ser | Serine     |
| H | His | Histidine     | T | Thr | Threonine  |
| I | Ile | Isoleucine    | V | Val | Valine     |
| K | Lys | Lysine        | W | Trp | Tryptophan |
| L | Leu | Leucine       | Y | Tyr | Tyrosine   |

BACKGROUND OF THE INVENTION

Most human leukemia are associated with chromosomal abnormalities resulting from genetic mutations or translocations that can create new hybrid genes capable of expressing mutated or fused proteins. The encoded abnormal fusion proteins are characterized by a joining region segment composed of a unique sequence of amino acids that is potentially immunogenic.

In chronic myelogenous leukemia (CML), the t(9;22) translocation results in a chimeric bcr-abl gene which encodes a 210 kD fusion protein. Two chimeric P210 bcr-abl proteins comprising products of either the b2a2 exon junction or the b3a2 exon junction can be alternatively expressed in CML cells. The junctional sequences represent unique tumor specific determinants, not only because they contain a joined set of amino acid sequences that are normally not expressed on the same protein, but also because at the exact fusion point, a codon for a new amino acid is present (1,2).

Similarly, a specific chromosomal translocation is present in acute promyelocytic leukemia (APL) cells which yield a 90–110 kD protein in which the product of the third exon of the RAR gene, located on chromosome 17, is fused to the amino terminal portion of a Zn-finger protein, PML from chromosome 15. Alternative breakpoints yield PML-RAR A and PML-RAR B that are observed in cells from 90% of APL patients (3,4). As with CML, both APL proteins contain an unique epitope consisting of the site of fusion in addition to a new amino acid.

Human T cell recognition of tumor associated antigens has been demonstrated for human melanoma antigens (5,6), as well as for a single point mutation in ras, resulting in a single amino acid change (7). Specific human CD4 T cell responses have been generated in vitro against the PML-RAR fusion protein found in APL cells (8), and in vivo, against B cell lymphoma immunoglobulin idiotypes (9).

The pairs of proteins found in CML and APL represent some of the most obvious targets for an immunological approach to the treatment of these leukemias and serve as a model for this approach in other neoplasms. Though the bcr-abl and PML-RAR proteins have an intracellular location, enzymatic degradation products of these fusion proteins could be presented on the cell surface as short peptides, 8–25 amino acids in length, within the cleft of HLA molecules, and potentially may be recognized by T cells. These peptides are derived by intracellular processing of exogenous and endogenous proteins as part of the antigen presentation pathway (10).

The amino acid motifs responsible for specific peptide-binding to HLA class I molecules have been determined for the common HLA class I types by the use of the analysis of acid-eluted naturally processed peptides and by use of cell lines defective in intracellular peptide loading and processing (11–13). More recently, a quantitative molecular radiobinding assay for the analysis of peptide binding to purified HLA class I molecules has been developed by Sette et al. (14).

In order to develop a vaccine strategy for APL and CML, the first two important questions are whether oncogenic fusion proteins contain suitable amino acid sequences and appropriate anchor motifs for binding to class I molecules and whether these breakpoint peptides can bind with sufficiently high affinity to the groove of HLA class I molecules; this activity is necessary to induce a leukemia specific T cell response. The ability of a series of synthetic peptides corresponding to the junctional sequences of bcr-abl and PML-RAR proteins to bind to purified human class I molecules is analyzed here. The rationale for this approach was twofold: 1) Breakpoint spanning peptides able to bind class I molecules could be potential candidate antigens for active immunotherapy against these leukemias. 2) Evidence that unique tumor specific breakpoint sequences are not presented in the context of HLA molecules would provide a molecular basis for immune non-responsiveness to abnormal intracellular fusion proteins in leukemic cells.

Cullis et al. (Leukemia (1994) 8:165–170), tested 18 peptides spanning the junctional sequences of the b2a2 and b3a2 protein for their ability to rescue the expression of the class I alleles in two human cell lines LBL 721.174 (T2) (HLA A2, B5) and BM 36.1 (HLA A1, B35). These cells are defective in intracellular peptide loading of class I molecules. None of the bcr-abl peptides enhanced HLA A2 or HLA B35 allele expression when compared with allele specific control peptides. The authors concluded that none of the CML peptides satisfies the known peptide-binding motifs for these alleles.

Gambacorti-Passerini, et al. was unable to demonstrate generation of a CD8/HLA class I restricted response to the fusion breakpoint peptides in acute promyelocytic leukemia (APL). (*Blood* (1994) 84(Suppl): p.618a, Abstract 2459).

Chen, et al. reported that immunization of mice with synthetic peptides corresponding to the BCR-ABL joining region elicited peptide-specific CD4+, class II major histocompatibility complex-restricted T cells. (Proc. Natl. Acad. Sci. USA (1992) 89: 1468–1472). Being human proteins, both BCR and ABL are foreign proteins to mice. Immunogenicity of a foreign peptide, even a foreign breakpoint peptide, does not directly address whether peptides spanning the joining region of two native proteins can stimulate an immunogenic response.

The data presented here is the first time that breakpoint peptides have been shown to be able to bind HLA class I molecules. In addition, such breakpoint peptides stimulated proliferation of human cytotoxic T-cells which demonstrated an ability to kill cells presenting the breakpoint peptide in the cleft of the appropriate HLA molecule.

SUMMARY OF THE INVENTION

This invention provides a method of identifying a fusion point-spanning peptide capable of specifically binding to a human major histocompatibility complex molecule, comprising: incubating the fusion point-spanning peptide with the major histocompatibility complex molecule and a labeled standard peptide which binds to the major histocompatibility complex molecule; and determining inhibition of binding of the standard peptide to the major histocompatibility complex molecule, thereby identifying the fusion point-spanning peptide capable of specifically binding to the major histocompatibility complex molecule.

This invention provides a method of identifying a fusion point-spanning peptide immunogenic to human immune cells, comprising: incubating the fusion point-spanning peptide with a major histocompatibility complex molecule and a labeled standard peptide which binds to the major histocompatibility complex molecule; and determining that the fusion point-spanning peptide has a binding affinity for the major histocompatibility complex molecule such that the concentration that inhibits binding of the standard peptide to the major histocompatibility complex molecule by fifty percent is about five hundred nanomolar or less, thereby identifying a fusion point-spanning peptide immunogenic to human immune cells.

This invention provides a pharmaceutical composition comprising a therapeutically effective amount of a fusion point-spanning peptide capable of binding to a major histocompatibility complex molecule and inducing an immune response in a subject.

DESCRIPTION OF THE FIGURES

FIG. 1A: The amino acid sequences surrounding the oncogenic fusion protein breakpoint CML b3a2. The uniqoe junctional amino acid is shown in bold. All possible 11 amino acid sequences are illustrated below the 21 amino acid sequence, as an example.

FIG. 1B: The amino acid sequences surrounding the oncogenic fusion protein breakpoint CML b2a2. The unique junctional amino acid is shown in bold.

FIG. 1C: The amino acid sequences surrounding the oncogenic fusion protein breakpoint PML-RARα A. The unique junctional amino acid is shown in bold.

FIG. 1D: The amino acid sequences surrounding the oncogenic fusion protein breakpoint PML-RARα B. The unique junctional amino acid is shown in bold.

FIG. 2: Specific proliferation of human T cells in response to stimulation with b3a2-CML peptide. Peripheral Blood Mononuclear (PBMC) cells from a healthy donor were stimulated as previously described (E. Celis, et al., "Induction of anti-tumor cytotoxic T lymphocytes in normal humans using primary cultures and synthetic peptide epitopes," Proc. Natl. Acad. Sci. USA (1994) 91: 2105–2109) with a b3a2-CML derived peptide, 25 amino acids in length. After two sets of stimulations (day 0 and day 12, using irradiated (black bars) or Paraformaldehyde-fixed (gray bars) b3a2-CML pulsed autologous PBMC as source of antigen presenting cells, T cells were incubated (day 19, 1:1 ratio) with autologous PBMC under 3 conditions: 1) not pulsed, 2) pulsed with b3a2-CML peptide or 3) pulsed with a control peptide (CDR2), 17 amino acids in length as shown in the figure. After 72 hours of culture, specific proliferation was measured by 3H-Thymidine incorporation. The data show specific proliferation of T cells incubated with b3a2-CML peptide-pulsed autologous PBMC as antigen presenting cells. No proliferation was observed when no peptide was added to the APCs or APCs where pulsed with the control peptide.

DETAILED DESCRIPTION OF THE INVENTION

Figure 3:
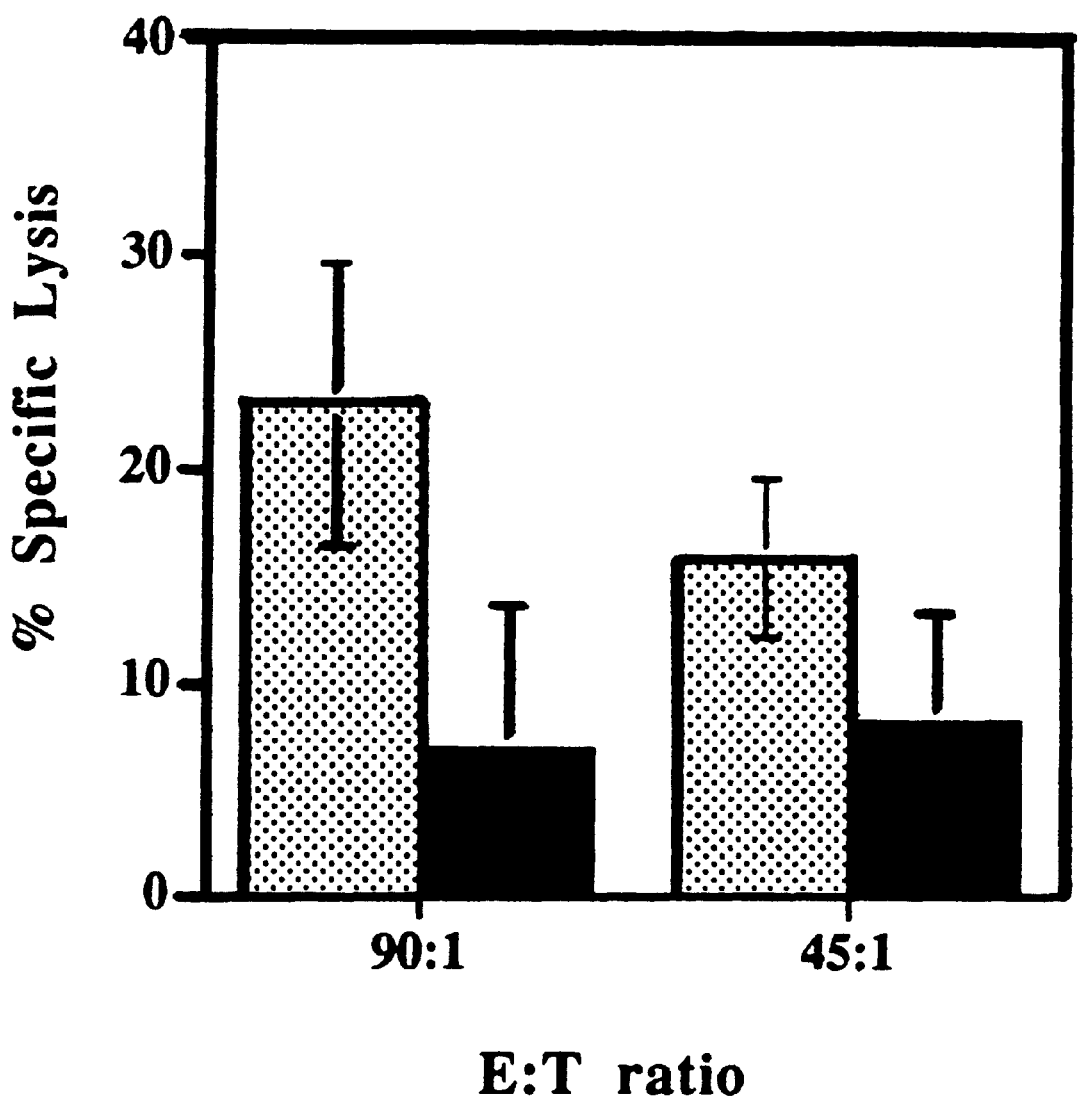
FIG. 3: CML-b3a2 specific T cells: cytotoxicity against b3a2-pulsed targets. Peripheral Blood Mononuclear Cells from an HLA A3 donor were stimulated as previously described (E. Celis, et al., Proc. Natl. Acad. Sci. USA (1994) 91: 2105–2109) with b3a2-CML peptide or an HIV-derived control peptide. This control peptide was previously shown to bind HLA A3 class I molecules and to elicite peptide-specific cytotoxic T lymphocytes in in vitro assays. Briefly, after two sets of stimulations (day 0 and day 12) with peptides, cells were incubated (day 19 for four hours) with 51Cr labeled autologous EBV transformed cells previously pulsed with b3a2-CML or HIV-A3 control peptide. Percent specific cytotoxicity was determined by calculating the percent specific 51Cr release: [(cpm of the test sample -cpm of the spontaneous 51Cr release)/(cpm of the maximal 51Cr release -cpm of the spontaneous 51Cr release)]×100. The spontaneous 51Cr release was determined by incubating the targets alone, in the absence of the effectors, and the maximal 51Cr release was obtained by incubating the targets with 2% SDS. The data show percent specific killing of b3a2-CML peptide (black bars) or control peptide (gray bars) pulsed targets by effector cells previously stimulated with b3a2-CML or control peptide at two different E:T ratios.

This invention provides a method of identifying a fusion point-spanning peptide capable of specifically binding to a human major histocompatibility complex molecule, comprising: incubating the fusion point-spanning peptide with the major histocompatibility complex molecule and a labeled standard peptide which binds to the major histocompatibility complex molecule; and determining inhibition of binding of the standard peptide to the major histocompatibility complex molecule, thereby identifying the fusion point-spanning peptide capable of specifically binding to the major histocompatibility complex molecule.

In an embodiment of this method, the fusion point-spanning peptide is an oncogenic fusion point-spanning peptide associated with a cancer. Translocations are common in many cancers, for example leukemia (e.g., chronic myelogenous leukemia, acute promyelocytic leukemia, and mixed-lineage leukemia) hematopoietic cancer, colorectal cancer, hepatocellular carcinoma, lymphoid neoplasms, lymphoma, lymphoproliferative disease and a tumor. Other cancers are known in the art. See, for example, Jeffrey Cossman, Molecular Genetics in Cancer Diagnosis (Elsevier, 1990 New York), and F. Mitelman, Catalog of Chromosome Aberrations in Cancer (Liss, New York 1988). Translocations occur in other conditions as well, for example c-myc translocations occur in Burkitt's lymphoma, and in association with AIDS. In a preferred embodiment, the peptide is associated with chronic myelogenous leukemia.

In an embodiment, the fusion point-spanning peptide has from about eight to about eleven amino acid residues. In preferred embodiments, the fusion point-spanning peptide has nine amino acid residues or eleven amino acid residues.

In an embodiment, the human major histocompatibility complex molecule is a HLA class I or HLA class II molecule. Specific examples of HLA class I molecules for use in this invention include, but are not limited to, HLA A1, HLA A2.1, HLA A3.2, HLA A11, HLA A24, HLA B7, HLA B8, and HLA B27. It is preferred that the HLA class I molecule is selected from the group consisting of: HLA A3.2, HLA A11, and HLA B8. In an embodiment, the fusion point-spanning peptide has a binding motif for the HLA class I or HLA class II molecule.

In an embodiment of this method, the standard peptide is labelled with a radioactive label. Many suitable radioactive labels are known to those of skill in the art, for example iodine-125.

In an embodiment, the concentration of the fusion point-spanning peptide that inhibits binding of the standard peptide by fifty percent is about five hundred nanomolar or less. "Affinity" or "binding affinity" of the fusion point-spanning peptide is defined as the $IC_{50}$ needed to inhibit binding of the standard peptide for each MHC molecule. In a more specific embodiment, the inhibitory concentration is about one hundred nanomolar or less. In another embodiment, the inhibitory concentration is at least about five nanomolar. Therefore, this invention also provides the above-described method wherein the inhibitory concentration (affinity) is between about five nanomolar and about five hundred nanomolar.

In addition to their use in vaccines and other in vivo and ex vivo therapeutic uses, the fusion-point spanning peptides of this invention can be used to detect the presence of the appropriate MHC molecule in a sample, and to quantitate the amount of the MHC molecule. Likewise, the MHC binding peptides of this invention can be used in competitive binding experiments to identify other peptides with binding affinity for MHC molecules, much as the "standard peptides" were used in Example 1 to identify binding affinity of the breakpoint peptides described herein.

This invention provides a method of identifying a fusion point-spanning peptide immunogenic to immune cells, comprising: incubating the fusion point-spanning peptide with a major histocompatibility complex molecule and a labeled standard peptide which binds to the major histocompatibility complex molecule; and determining that the fusion point-spanning peptide has a binding affinity for the major histocompatibility complex molecule such that the concentration that inhibits binding of the standard peptide to the major histocompatibility complex molecule by fifty percent is about five hundred nanomolar or less, thereby identifying a fusion point-spanning peptide immunogenic to immune cells. Preferably the immune cells are human immune cells, for example human T cells.

In a further embodiment of the method of identifying a fusion point-spanning peptide immunogenic to immune cells comprises incubating the fusion-point spanning peptide having an affinity of five hundred nanomolar or less with the human immune cells; and observing induction of the human immune cells. This step can be performed at any point in the above-described method. Alternatively, incubating the fusion-point spanning peptide having an affinity of five hundred nanomolar or less with the human immune cells; and observing induction of the human immune cells is itself a complete method for identifying a fusion point-spanning peptide immunogenic to immune cells.

In an embodiment, the human immune cells are T cells and the induction is induction of cytotoxic T lymphocytes. In an embodiment, the fusion point-spanning peptide is an oncogenic fusion point-spanning peptide associated with a cancer. For example, the peptide may be associated with leukemia, hematopoietic cancer, and a tumor, as well as others known to those of skill in the art. In a preferred embodiment, the leukemia is chronic myelogenous leukemia.

In an embodiment, the fusion point-spanning peptide has from about eight to about eleven amino acid residues. In preferred embodiments, the fusion point-spanning peptide has nine amino acid residues or eleven amino acid residues.

In an embodiment, the human major histocompatibility complex molecule is a HLA class I or HLA class II molecule. Specific examples of HLA class I molecules for use in this invention include, but are not limited to, HLA A1, HLA A2.1, HLA A3.2, HLA A11, HLA A24, HLA B7, HLA B8, and HLA B27. It is preferred that the HLA class I molecule is selected from the group consisting of: HLA A3.2, HLA A11, and HLA B8. Suitable HLA class II molecules include, but are not limited to, a HLA DR molecule, for example HLA DR11. In an embodiment, the fusion point-spanning peptide has a binding motif for the HLA class I or HLA class II molecule.

In an embodiment of this method, the standard peptide is labelled with a radioactive label. Many suitable radioactive labels are known to those of skill in the art, for example iodine-125.

In a preferred embodiment, the inhibitory concentration, or binding affinity, is about one hundred nanomolar or less. In an embodiment, the inhibitory concentration is between about five nanomolar and about five hundred nanomolar.

This invention provides a method of inducing human cytotoxic T cells, comprising contacting a human T cell with a fusion point-spanning peptide capable of specifically binding to a human major histompatibility complex molecule. In an embodiment, the human T cell is CD8+, CD4+, or both CD8+, CD4+.

In an embodiment of this method, the fusion point-spanning peptide is a fusion point-spanning peptide associated with a cancer, for example leukemia, hematopoietic cancer, and a tumor. In a preferred embodiment, the peptide is associated with chronic myelogenous leukemia.

In an embodiment, the fusion point-spanning peptide has from about eight to about eleven amino acid residues. In preferred embodiments, the fusion point-spanning peptide has nine amino acid residues or eleven amino acid residues. In specific embodiments, the fusion point-spanning peptide is selected from the groups consisting of: ATGFKQSSK (SEQ ID NO:28); GFKQSSKAL (SEQ ID NO:30); KQSSKALQR (SEQ ID NO:32); and HSATGFKQSSK (SEQ ID NO:2).

In an embodiment, the human major histocompatibility complex molecule is a HLA class I or HLA class II molecule. Specific examples of HLA class I molecules for use in this invention include, but are not limited to, HLA A1, HLA A2.1, HLA A3.2, HLA A11, HLA A24, HLA B7, HLA B8, and HLA B27. It is preferred that the HLA class I molecule is selected from the group consisting of: HLA A3.2, HLA A11, and HLA B8. Suitable HLA class II molecules include, but are not limited to, a HLA DR molecule, for example HLA DR11. In an embodiment, the fusion point-spanning peptide has a binding motif for the HLA class I or HLA class II molecule.

In an embodiment of this method, the standard peptide is labelled with a radioactive label. Many suitable radioactive labels are known to those of skill in the art, for example iodine-125.

In an embodiment, the concentration of the fusion point-spanning peptide that inhibits binding of the standard peptide by fifty percent is about five hundred nanomolar or less. "Affinity" or "binding affinity" of the fusion point-spanning peptide is defined as the $IC_{50}$ needed to inhibit binding of the standard peptide for each MHC molecule. In a more specific embodiment, the inhibitory concentration is about one hundred nanomolar or less. In an embodiment, the inhibitory concentration is between about five nanomolar and about five hundred nanomolar.

Antigenic breakpoint peptides may be used to elicit CTL ex vivo. The resulting CTL, can be used to treat the condition associated with a fusion protein, such as chronic infections (viral or bacterial) or tumors in patients that do not respond to other conventional forms of therapy, or will not respond to a peptide vaccine approach of therapy. Ex vivo CTL responses to a particular pathogen (infectious agent or tumor antigen) are induced by incubating in tissue culture the patient's CTL precursor cells (CTLp) together with a source of antigen-presenting cells (APC) and the appropriate immunogenic peptide. After an appropriate incubation time (typically 1–4 weeks), in which the CTLp are activated and mature and expand into effector CTL, the cells are infused back into the patient, where they will destroy their specific target cell (typically an infected cell or a tumor cell).

This invention provides a pharmaceutical composition comprising a therapeutically effective amount of a fusion point-spanning peptide capable of binding to a major histocompatibility complex molecule and inducing an immune response in a subject.

In an embodiment of this method, the fusion point-spanning peptide is an oncogenic fusion point-spanning peptide associated with a cancer, for example leukemia, hematopoietic cancer, and a tumor. In a preferred embodiment, the peptide is associated with chronic myelogenous leukemia.

In an embodiment, the fusion point-spanning peptide has from about eight to about eleven amino acid residues. In preferred embodiments, the fusion point-spanning peptide has nine amino acid residues or eleven amino acid residues. In specific embodiments, the fusion point-spanning peptide is selected from the groups consisting of: ATGFKQSSK (SEQ ID NO:28); GFKQSSKAL (SEQ ID NO:30); KQSSKALQR (SEQ ID NO:32); and HSATGFKQSSK (SEQ ID NO:2).

In an embodiment, the human major histocompatibility complex molecule is a HLA class I or HLA class II molecule. Specific examples of HLA class I molecules for use in this invention include, but are not limited to, HLA A1, HLA A2.1, HLA A3.2, HLA A11, HLA A24, HLA B7, HLA B8, and HLA B27. It is preferred that the HLA class I molecule is selected from the group consisting of: HLA A3.2, HLA A11, and HLA BB. Suitable HLA class II molecules include, but are not limited to, a HLA DR molecule, for example HLA DR11. In an embodiment, the fusion point-spanning peptide has a binding motif for the HLA class I or HLA class II molecule.

In an embodiment, the pharmaceutical composition further comprises a pharmaceutically acceptable carrier, an adjuvant, or both. In a preferred embodiment the adjuvant is QS21.

The pharmaceutical composition may be formulated for administration by any of the many techniques known to those of skill in the art. For example, this invention provides for administration of the pharmaceutical composition parenterally, intravenously, subcutaneously, intradermally, intramucosally, topically, orally, or by inhalation.

This invention provides a method of inducing an immune response in a subject, comprising administering to the subject an effective amount of the pharmaceutical composition. In specific embodiments, the immune response is a CD8/HLA class I immune response or a CD4/HLA class II immune response. In an embodiment, the subject is a mammal, for example a mouse, rat, rabbit, hamster, guinea pig, horse, cow, sheep, goat, pig, cat, dog, monkey, ape or human. Preferably, the subject is a human.

This invention also provides a method of immunizing a subject a gainst a condition associated with a fusion protein, comprising administering an effective amount of the pharmaceutical composition. In an embodiment, the subject is a mammal, f or example a mouse, rat, rabbit, hamster, guinea pig, horse, cow, sheep, goat, cat, pig, dog, monkey, ape or human. Preferably, the subject is a human.

As used herein, "immunizing" and aimmunization encompass both full and partial immunization. Accordingly, in an embodiment of this method, the subject becomes partially immune to the condition. In another embodiment, the subject becomes fully immune to the condition.

A vaccine can be constructed by way of combination of the peptide with a suitable adjuvant (Allison, et al., "Adjuvant formulations and their mode of action" Semin. Immun. (1990) 2:369). Adjuvants such as incomplete Freund's adjuvant, aluminum phosphate, aluminum hydroxide, QS21, BCG or alum are materials well known in the art. Multiple injections (from 2 to 10) are likely to be necessary to achieve an adequate response.

In an embodiment, the condition is a cancer, for example leukemia, hematopoietic cancer, and a tumor. In a preferred embodiment, the subject is immunized against chronic myelogenous leukemia.

The method of immunization of this invention can be performed on a subject who has not developed the condition. In such a case, the subject is preferably someone who is at risk for developing the disease. A determination as to risk can be made on the basis of family history, genetic screening, behavioral risk factors, environmental risk factors, and other relevant considerations known to those of skill in the art. Alternatively, the method of immunization may be preformed on a subject who has the condition and in whom the condition is active, or on one in whom the condition is in remission.

The peptide may be administered into the subject linked to its own carrier or as a hompolymer or heteropolymer of active peptide units. Such a polymer has the advantage of increased immunological reaction and, where different peptides are used to make up the polymer, the additional ability to induce antibodies and/or CTLs that react with different antigenic determinants of condition, e.g. the virus or tumor cells. Useful carriers are well known in the art, and include, e.g., thyroglobulin, albumins such as human serum albumin, tetanus toxoid, polyamino acids such as poly (lysine:glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. And, CTL responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amount of CTLs specific for the desired antigen, and the host becomes at least partially immune to later infection, or resistant to developing chronic infection.

The precise amounts depend on the patient's state of health and weight, the mode of administration, the nature of the formulation, etc., but generally range from about 1.0 μg to about 5000 μg per 70 kilogram patient, more commonly from about 10 μg to about 500 μg mg per 70 kg of body weight.

An alternative approach available to vaccinate includes introduction of the genetic sequence that encodes the peptides into an appropriate vector (Tindle, R. W. et al. *Virology* (1994) 200:54) or as naked DNA (Nabel, et al. PNAS-USA (1990) 90: 11307) administered by means of a gene gun, to elicit a response, and the use of a carrier. For example, the peptides of this invention can be expressed by attenuated viral hosts, such as vaccinia or fowlpox. This approach involves the use of vaccinia virus as a vector to express nucleotide sequences that encode the peptides of the invention. Upon introduction into an acutely or chronically infected host or into a non-infected host, the recombinant vaccinia virus expresses the immunogenic fusion point-spanning peptide, and thereby elicits a host CTL response. Vaccinia vectors and methods useful in immunization protocols are described in, e.g., U.S. Pat. No. 4,722,848, incorporated herein by reference. Another vector is BCG (Bacille Calmette Guerin). BCG vectors are described in Stover et al. (*Nature* 351:456–460 (1991)). A wide variety of other vectors useful for therapeutic administration or immunization of the peptides of the invention, e.g., *Salmonella typhi* vectors and the like, will be apparent to those skilled in the art from the description herein.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

EXAMPLE 1

Specific Binding of Leukemia Oncogene Fusion Protein Peptides to HLA Class I Molecules Materials and Methods Peptides. A series of peptides 8–11 amino acids in length, spanning the b3a2 and b2a2 junctional regions of bcr-abl and the type A and B of PML-RAR were synthesized on the basis of the published amino acid sequences (2,4) by Chiron/Mimotopes. Standard peptides known to bind efficiently to HLA A1, A2.1, A3.2, A11, A24, B7, B8, B27 were synthesized and $^{125}$I-labeled by Cytel, San Diego, Calif. as described (14,15). Peptide purity was estimated >90% by high performance liquid chromatography (HPLC).

Purification of HLA class I molecules. HLA class I molecule purification was performed according to the procedure recently described by Sette et al. (14,15). Briefly, after preparation of detergent lysed extracts from EBV cell lines homozygous for each HLA type used in the study, HLA molecules were purified by affinity chromatography. HLA molecules were concentrated and purity was determined to be >90% by SDS-polyacrylamide gel electrophoresis.

MHC binding assay. Peptide binding to purified MHC class I molecules was measured as described (14,15). Briefly, the assay is based on the inhibition of binding of the radiolabeled standard peptide described above to detergent solubilized purified MHC molecules. HLA concentrations (about 10 nM) yielding 15% bound standard peptide were used in the inhibition assay. A serial dilution of CML or APL breakpoint spanning peptide (30 uM to 1 nM) were incubated together with 5 Mn of the radiolabeled standard peptide and matched appropriate HLA molecule. The percent MHC-bound radioactivity was then determined by gel filtration, and the inhibition calculated.

Results

Analysis of HLA class I motifs. CML: A total of 76 possible peptide sequences spanning 8, 9, 10 or 11 amino acids of the b2a2 and b3a2 junctional regions of bcr-abl proteins were analyzed for motifs with potential to bind to the most common HLA-A class I molecules (A1, A2.1, A3.2, A11, A24) and HLA-B molecules in which anchor motifs are known (B7, B8 and B27) (16–22). These HLA types are amongst the predominant types expressed in the United States population. The sequences of all peptides 11 amino acids in length encompassing the b3a2 breakpoints are shown (FIG. 1A). Series of peptides 8, 9 and 10 amino acids in length were included in the analysis for MHC binding as well. The sequence of the b2a2 breakpoint is also shown (FIG. 1B). Based on their sequences alone, 21 bcr-abl peptides (10 for the b2a2 breakpoint and 11 for the b3a2 breakpoint) of 8, 9, or 10 amino acids in length were predicted to have the potential of binding one or more class I molecule (Table 1).

TABLE 1

Binding Affinities of CML Peptides to HLA Class I Molecules

| SEQ ID NO | SOURCE | SEQUENCE | HLA MOTIF | AFFINITY (nM) | | | | | | |
|---|---|---|---|---|---|---|---|---|---|---|
| | | | | A2.1 | A3.2 | A11 | A24 | B7 | B8 | B27 |
| | b2a2 | | | | | | | | | |
| 17 | 1 | IPLTINKEEAL | B7 | | | | | — | | |
| 18 | 2 | PLTINKEEA | A2.1 | — | | | | | | |
| 19 | 3 | PLTINKEEAL | A2.1 | — | | | | | | |
| 20 | 4 | LTINKEEAL | A2.1, B8 | — | | | | | 1900 | |
| 21 | 5 | LTINKEEALQR | A3.2, A11 | | — | 5450 | | | | |
| 22 | 6 | TINKEEAL | A2.1 | — | | | | | | |
| 23 | 7 | TINKEEALQR | A3.2, A11 | | — | — | | | | |
| 24 | 8 | INKEEALQR | A11 | | | — | | | | |
| 25 | 9 | NKEEALQR | B27 | | | | | | | — |
| 26 | 10 | EALQRPVASDF | A24 | | | | — | | | |
| | b3a2 | | | | | | | | | |
| 2 | 1 | HSATGFKQSSK | A3.2, A11 | | 400 | 125 | | | | |
| 27 | 2 | SATGFKQSSK | A3.2, A11 | | 5450 | 3530 | | | | |
| 28 | 3 | ATGFKQSSK | A3.2, A11 | | 300 | 97 | | | | |
| 4 | 4 | ATGFKQSSKAL | A2.1, B8 | — | | | | | 3600 | |
| 29 | 5 | TGFKQSSK | A3.2, A11 | | — | — | | | | |

TABLE 1-continued

Binding Affinities of CML Peptides to HLA Class I Molecules

| SEQ ID NO | SOURCE | SEQUENCE | HLA MOTIF | AFFINITY (nM) | | | | | | |
|---|---|---|---|---|---|---|---|---|---|---|
| | | | | A2.1 | A3.2 | A11 | A24 | B7 | B8 | B27 |
| 30 | 6 | GFKQSSKAL | B8 | | | | | | 190 | |
| 6 | 7 | GFKQSSKALQR | A3.2, A11 | | 810 | 2150 | | | | |
| 31 | 8 | FKQSSKALQR | A3.2, A11 | | 545 | 5000 | | | | |
| 32 | 9 | KQSSKALQR | A3.2, A11 | | 43 | 273 | | | | |
| 33 | 10 | QSSKALQR | A3.2, A11 | | — | — | | | | |
| 12 | 11 | KALQRPVSDF | A24 | | | | — | | | |

A dash indicates that the value was greater than 30 μM.

APL: The 76 peptides of appropriate lengths spanning PML-RAR A and B fusion regions were also studied. The sequences surrounding the two breakpoints are shown (FIGS. 1C, D). Peptides 8, 9, 10 and 11 amino acids in length were analyzed for the presence of specific HLA class I anchor motifs. Two peptides from PML-RAR A and 2 from PML-RAR B breakpoint were considered potentially suitable for class I binding based on the presence of specific motifs (Table 2).

TABLE 2

Binding Affinities of APL Peptides to HLA Class I Molecules

| SEQ ID NO | SOURCE | SEQUENCE | HLA Motif | AFFINITY (nM) A2.1 |
|---|---|---|---|---|
| | PML-RARαA | | | |
| 34 | 1 | HVASGAGEAAI | A2.1 | — |
| 35 | 2 | VASGAGEAAI | A2.1 | — |
| | PML-RARαB | | | |
| 36 | 1 | DLSSCITQGKA | A2.1 | — |
| 37 | 2 | CITQGKAI | A2.1 | — |

A dash indicates that the value was greater than 50 μM.

Peptide synthesis and MHC binding assay. CML: The CML peptides with appropriate motifs were synthesized and tested for binding to purified HLA molecules. Among the 11 b3a2 peptides selected for HLA motifs, 6 displayed significant binding affinities for both HLA A3.2 and A11 (Table 1). These two class I molecules have many similarities in structure and share similar binding motifs (19). The peptide ATGFKQSSK (SEQ ID NO:28) bound with high affinity (<100 nM to achieve 50% inhibition) to HLA A11 and with intermediate affinity (100–500 Mn required for 50% inhibition) to HLA A3.2. In contrast, peptide KQSSKALQR (SEQ ID NO:32) showed high affinity binding to HLA A3.2 (43 Mn for 50% inhibition) and had intermediate affinity for HLA A11 (273 Mn). A third peptide HSATGFKQSSK (SEQ ID NO:2) was found to bind with intermediate affinity to both A3.2 and A11 (400 Mn and 125 nM for 50% inhibition, respectively). The remaining 3 peptides bound A3.2 or A11 much more weakly (>500 nM to <6 uM to achieve 50% inhibition). In addition, two b3a2 peptides bound to HLA B8 with intermediate (GFKQSSKAL (SEQ ID NO:30), 190 nM) or low affinity.

None of the 10 peptides belonging to the b2a2 breakpoint showed high or intermediate relative binding affinity (<500 Mn affinity) for any of the purified HLA class I molecules utilized in the binding assay. Two peptides displayed low affinity for HLA A11 or B8, respectively.

APL: Four APL sequences that contained motifs with potential for HLA binding to HLA A2.1 were synthesized and assayed as described. None of these peptides showed appreciable binding affinity for HLA A2.1 in the competitive assays (>50 uM for 50% inhibition) (Table 2).

Discussion

Among all 76 possible peptides spanning the breakpoints of the CML fusion proteins, there were 21 peptide sequences with potential HLA binding motifs; four peptides, all derived from the b3a2 breakpoint of bcr-abl, bound with either intermediate and high affinity to purified HLA A3.2 A11 and B8 molecules. This is the first time that leukemia-oncogene derived breakpoint peptides have been shown to be able to bind HLA class I molecules and provides a rationale for a therapeutic vaccine.

The bcr-abl and PML-RAR breakpoint-derived peptides are an ideal model system in which to explore active specific immunotherapy of cancer. These peptides represent potential antigens by virtue of the novel sequence of the junctional regions. Second, the sequences are found only in cells belonging to the leukemic clone. As both fusion proteins are involved in the leukemogenic events in these respective leukemias, antigen negative clonogenic cells are likely to be rare; thus escape by protein (antigen) loss is not probable. Finally, development of an active response specific to the antigen is not likely to be harmful, as the target is unique to the leukemia cells.

Because of their intracellular location, these fusion proteins may be processed and presented on the cell surface via the HLA class I molecule pathway and thus may be accessible to cytotoxic CD8 cells. Screening these peptides for HLA class I anchor motifs and testing them for effective HLA binding represents a first necessary step in the analysis of their value as potential antigens. Experiment 2 (below) illustrates the ability of HLA binding peptides to elicit class I restricted CD8 cells.

Data presented in Example 2 support the hypothesis that peptides that bind to HLA with moderate to high-affinity are those which are capable of T-cell stimulation after natural processing and cell surface presentation within stimulation of T cells is supported by additional evidence: 1) Naturally processed peptides that are found on the surface of live cells bound to HLA molecules typically have an affinity in the range described here for the CML peptides (19). 2) Only peptides that bind to HLA with affinities in this range were able to induce a cytotoxic response in vitro and in vivo models (24,25). 3) Peptides from the intracellular protein MAGE in melanoma identified by motifs as described above were found to be naturally expressed in the context of appropriate HLA molecules (26).

It is of considerable interest that no potential peptide antigens were found for APL or the CML fusion-peptide b2a2. This strongly suggests that specific CD8 responses restricted by the HLA types studied are unlikely in patients with APL or in the patients with CML and b2a2 breakpoint. Gambacorti-Passerini et al. (8) have shown, however that cytotoxic CD4 cells can be generated in vitro to longer APL derived fusion-peptides. Therefore, specific immunity should still be possible via class II responses. In addition, the results presented here provide a way for identifying other HLA A, B and C class I types that are capable of presenting specific APL or CML derived peptides.

Recent studies in patients with CML who have relapsed after an allogeneic bone marrow transplant, have demonstrated that infusion of donor T cells can reinduce durable complete responses. This observation shows that an immune response to CML can occur (27).

EXAMPLE 2

Specific Proliferation of Human T Cells in Response to Stimulation with b3a2-CML Peptide Human cells immunologically recognize breakpoint proteins and proliferate in response. Peripheral Blood Mononuclear (PBMC) cells from a healthy donor were stimulated as previously described (E. Celis, et al., "Induction of anti-tumor cytotoxic T lymphocytes in normal humans using primary cultures and synthetic peptide epitopes," Proc. Natl. Acad. Sci. USA (1994) 91: 2105–2109) with a b3a2-CML derived peptide, 25 amino acids in length IVHSATG-FKQSSKALQRPVASDFEP (SEQ ID NO:34). After two sets of stimulations (day 0 and day 12, using irradiated (black bars) or Paraformaldehyde-fixed (gray bars) b3a2-CML pulsed autologous PBMC as source of antigen presenting cells, T cells were incubated (day 19, 1:1 ratio) with autologous PBMC under 3 conditions: 1) not pulsed, 2) pulsed with b3a2-CML peptide or 3) pulsed with a control peptide (CDR2), 17 amino acids in length as shown in the figure. After 72 hours of culture, specific proliferation was measured by 3H-Thymidine incorporation. The data show specific proliferation of T cells incubated with b3a2-CML peptide-pulsed autologous PBMC as antigen presenting cells. No proliferation was observed when no peptide was added to the APCs or APCs where pulsed with the control peptide. (See FIG. 2).

Peptides that bind to HLA with moderate to high affinity are those which are capable of T-cell stimulation after natural processing and cell surface presentation within the cleft of the appropriate HLA. The importance of these moderate to high affinity peptides for effective stimulation of T cells is supported by additional evidence (15–23): (1) Naturally processed peptides that are found on the surface of live cells bound to HLA molecules typically have an affinity in the range described here for the CML peptides. (2) Only peptides that bind to HLA with affinities in this range were able to induce a cytotoxic response in vitro and in vivo models. (3) Peptides from the intracellular protein MAGE in melanoma identified by motifs as described above were found to be naturally expressed in the context of appropriate HLA molecules (26).

EXAMPLE 3

CML-b3a2 Specific T Cells: Cytotoxicity Against b3a2-pulsed Targets

Effector cells stimulated by breakpoint peptides as described in Example 3 kill target cells which present the breakpoint peptide presented in the cleft of HLA molecules. Peripheral Blood Mononuclear Cells from an HLA A3 donor were stimulated as previously described (E. Celis, et al., Proc. Natl. Acad. Sci. USA (1994) 91: 2105–2109) with b3a2-CML peptide KQSSKALQR (SEQ ID NO:32) or an HIV-derived control peptide. This control peptide was previously shown to bind HLA A3 class I molecules and to elicite peptide-specific cytotoxic T lymphocytes in in vitro assays. Briefly, after two sets of stimulations (day 0 and day 12) with peptides, cells were incubated (day 19 for four hours) with 51Cr labeled autologous EBV transformed cells previously pulsed with b3a2-CML or HIV-A3 control peptide. Percent specific cytotoxicity was determined by calculating the percent specific 51Cr release: [(cpm of the test sample -cpm of the spontaneous 51Cr release)/(cpm of the maximal 51Cr release -cpm of the spontaneous 51Cr release)]×100. The spontaneous 51Cr release was determined by incubating the targets alone, in the absence of the effectors, and the maximal 51Cr release was obtained by incubating the targets with 2% SDS. The data show percent specific killing of b3a2-CML peptide (black bars) or control peptide (gray bars) pulsed targets by effector cells previously stimulated with b3a2-CML or control peptide at two different E:T ratios. (See FIG. 3).

EXAMPLE 4

Vaccination of Patients with Chronic Myelogenous Leukemia with Tumor-Specific Breakpoint Peptides Adjuvant The most important reason for the poor host response against most tumor antigens is that tumor antigens are simply poor immunogens, primarily because they are autoantigens and may be tolerated immunologically. While classical immunological tolerance results from deletion of autoreactive B and T cells during early development, it is clear that many B and T cells capable of reacting against autoantigens in tumors are present in patients with melanoma though they rarely induce autoimmunity. Mechanisms described to explain this include ineffectual antigen presentation, peripheral B and T cell anergy and inability of the tumor cell to induce a "second signal" which is required to effectively activate T cells.

Immunization against CML peptides is done using the immunological adjuvant QS-21. Vaccines containing various protein antigens plus QS-21 have been described to induce cytotoxic T cells against target cells expressing these antigens (24–27).

QS-21 is an immune adjuvant designed to boost immune responses. QS-21 is a carbohydrate extracted from the bark of the South American tree Quillaja saponaria Molina. The monosaccharide composition, molecular weight, adjuvant effect and toxicity for a series of the saponins has been described. QS-21 has been selected due to its adjuvanticity and lack of toxicity. It has proven safe and relatively nontoxic at the dose level proposed and highly effective at augmenting the immunogenicity of an FeLV subunit vaccine in cats and an HIV-1 recombinant vaccine in Rhesus monkeys (25,26). Vaccines containing various proteins plus QS-21 have also been reported to induce cytotoxic T cells against targets expressing these antigens (26).

Therapeutic Agent

CML Class I Peptides: The four peptides, 9 and 11 amino acids long, have been synthesized on F-MOC solid phase synthesis and purified by HPLC. Purity has been assessed by amino acid sequence analysis by mass spectrometry. The sequence has been verified by mass spectrometry.

CML Class II Peptide: A single peptide, 25 amino acids long, has been synthesized on F-MOC solid phase synthesis and purified by HPLC. Purity has been assessed by amino acid sequence analysis by mass spectrometry. The sequence has been verified by mass spectrometry.

The amino acid sequences are:
1. ATGFKQSSK (SEQ ID NO:28)
2. KQSSKALQR (SEQ ID NO:32)
3. HSATGFKQSSK (SEQ ID NO:2)
4. GFKQSSKAL (SEQ ID NO:30)
5. IVHSATGFKQSSKALQRPVASDFEP (SEQ ID NO:34)

Vaccine Preparation and Testing

Endotoxin content is assayed by limulus assay and demonstrated to be less than 0.3 U/ml. Sterility IS confirmed by absence of bacterial growth on agar plates. Mycoplasma assays are negative. Moreover, general safety is confirmed in mice and guinea pigs.

Vaccine preparation: 10 ug, 30 ug, 100 ug, or 300 ug of each peptide (50,150,500,1500 of total peptide) is mixed with 100 ug of QS-21 in 0.5 ml PBS (Phosphate buffered saline, pH 7.4) and vialed. Vaccine is stored frozen below −20° C. The QS-21 is a product of Cambridge Biotech Corporation, Worcester, Mass., and is used under IND.

Treatment and Evaluation Schema

A3, -A11, or -B8 may be added to the MTD level (or maximum level if MTD is not reached) until a total of 14 patients with one of these HLA types has been evaluable at that level. No patients without these HLA types are accrued at the end of escalation. If at any time, the group of patients at this level shows a greater than 30% incidence of DLT, no additional patients are added. In this way the safety of the vaccine can be addressed, the MTD can be better defined, and a measure of the vaccine's possible activity can be assessed in patients most likely to respond. With 4 possible dosages, this escalation scheme takes a minimum of 2 patients and a maximum of 36 patients. Based on the prevalence of the relevant HLA types and the expected lack of toxicity, it is anticipated that 25 patients will accrue onto the study.

Risks

Autoimmune or hypersensitivity reactions to components of the vaccine or to skin test antigens are theoretical possibilities. The expression of the complete peptide sequence is believed to be restricted to leukemia cells only. Therefore, autoimmune reactions are considered to be unlikely.

TABLE 3

| | | WEEKS | | | | | |
|---|---|---|---|---|---|---|---|
| | Pre | 0 | 2 | 4 | 6 | 10 | 12 |
| TREATMENT | | | | | | | |
| VACCINATIONS | | X | X | X | X | X | |
| CLINICAL FOLLOW-UP | | | | | | | |
| PHYSICAL EXAM | X | X | LIMITED | LIMITED | LIMITED | LIMITED | LIMITED |
| CHEST X-RAY | X | | | | | | |
| SCREENING PROFILE | X | | X | | X | | X |
| CBC/DIFF | X | X | X | X | X | X | X |
| BM ASPIRATE | X | | | | | | X |
| CYTOGENETICS | X | | | | | | X* |
| HLA TYPING | X | | | | | | |
| PCR FOR bcr/abl | X | | | | | | X* |
| RESEARCH ASSAYS | | | | | | | |
| SEROLOGY | | X | | | X | | X |
| PROLIFERATION | | X | | | X | | X |
| CYTOTOXICITY | | X | | | X | | X |
| DELAYED HYPERSENSITIVITY | | X | | | X | | X |

*Genetics and PCR are done if the patient is in clinical remission

Treatment

Five vaccinations are administered over a 10 week period. The first group of patients receives 50 ug of peptide per dose, the subsequent groups receive 150, 500, or 1500 ug of peptide per dose, respectively. (As there are five peptides, the total dose of each peptide per injection is 10 ug at the first level, and so on.) All vaccinations are administered subcutaneously with vaccinations sites rotated between extremities. There is no escalation within a group. Patients are observed for 2 hours after vaccination. Two weeks after the last vaccination patients are reevaluated.

Dose Escalation Scheme

Dose limiting toxicity (DLT) is defined as any grade 4 toxicity. If no instance of DLT is observed among the initial three patients placed on a dosage level, the dosage is escalated for the successive group of three patients. If one instance of DLT, out of three patients is observed for a given dosage level, 3 additional patients are treated at that level. If 2 instances of DLT are observed any level, dose escalation is stopped. The MTD is defined as the highest dose level where no more than one instance of DLT is observed. At the end of the study escalation, additional patients with HLA- Expected toxicity with this dose of QS-21 includes mild local inflammation at injection sites and occasional fever.

Criteria for toxicity: Toxicity is graded in accordance with the common toxicity criteria developed by the National Cancer Institute.

Patient Evaluation

Within 2 weeks of study, patient has a chest x-ray, complete physical exam, screening profile, CBC with differential, bone marrow aspirates for morphology, and electrolytes. Cytogenetics and PCR for bcr/abl breakpoint type, must have been obtained and results available before entry. A CBC is done at the time of first vaccination. Complete HLA typing for HLA-A, -B, Dr must be available before entering during the phase II section of the trial.

Serological Response: Peripheral blood (10 ml) is drawn immediately before the first and fourth vaccination (6 weeks), and then 2 weeks after the last vaccination (12 weeks). The patients' sera is tested by ELISA for antibodies against CML peptides and related antigens. Patients with titers shown by ELISA to react specifically with CML are considered serologic responders. If serology is positive, a 10 ml sample may be drawn at 1,3, and 6 months after the last vaccination.

Lymphocyte Response. Peripheral blood (up to 150 ml) is drawn prior to treatment and at 6 and 12 weeks during treatment as indicated in Table 3. If T cell reactivity is induced, one additional sample may be drawn at 6–10 weeks after the last vaccination to determine the duration of this reactivity. Peripheral blood lymphocytes (PBLs) are tested for proliferation, cytotoxicity, and precursor frequency.

Delayed type hypersensitivity. DTH against the peptides (10 ug per test dose) individually is measured before the first vaccination, and at 6 and 12 weeks. Control DTH tests also include mumps and trichophyton.

Clinical Course: Patients are evaluated at the time of each vaccination and at 2 weeks after the last vaccination. Screening profile, CBC, and differential are performed at the time of the second and fourth vaccinations and 2 weeks after the sixth vaccination. Cytogenetics and PCR analysis for breakpoints are evaluated for patients in complete hematologic remission at 12 weeks, or at the end of study. If negative, as clinically indicated thereafter. Patients in hematologic remission have a bone marrow aspirate done on week 12, or at the end of study and thereafter as clinically indicated.

REFERENCES

REFERENCES FOR BACKGROUND AND EXAMPLE 1

1. Kurzrock R., J. U. Gutterman, and M. Talpaz. 1988. The molecular genetics of the Philadelphia chromosome-positive leukemias. N. Engl. J. Med. 319:990.

2. Grosveld G., T. Verwoerd, T. van Agthoven, A. de Klein, K. L. Ramachandran, N. Heisterkamp, K. Stam, and J. Groffen. 1986. The chronic myelocytic cell line K562 contains a breakpoint in bcr and produces a chimeric bcr-abl chimeric transcript. Mol. Cell. Biol. 6:607.

3. Rowley J. D., H. M. Golomb, and C. Doigherty. 1977. 15/17 translocation, a consistent chromosomal change in acute promyelocytic leukemia. Lancet 1:549.

4. de The' H., C. Chomienne, M. Lanotte, L. Degos, and A. Dejean. 1990. The t(15;17) translocation of acute promyelocytic leukemia fuses the retinoic acid receptor alpha gene to a novel transcribed locus. Nature 347:558.

5. van der Bruggen P., C. Traversari, P. Chomez, C. Lurquin, E. De Plaen, B. van den Eynde, A. Knuth, and T. Boon. 1991. A gene encoding an antigen recognized by cytolytic T lymphocytes on a human melanoma. Science 254:1643.

6. Traversari C., P. van der Bruggen, I. F. Lenscher, C. Lurquin, P. Chomez, A. van Pel, E. De Plean, A. Amar-Cortesec, and T. Boon. 1992. A nonapeptide encoded by human gene MAGE-1 is recognized on HLA-A1 by cytolytic T lymphocytes directed against tumor antigen MZ2-E. J. Exp. Med. 176:1453.

7. Jung S., and H. J. Schiusener. 1991. Human T lymphocytes recognize a peptide of single point-mutated, oncogenic ras proteins. J. Exp. Med. 173:273.

8. Gambacorti-Passerini C., F. Grignani, F. Arienti, P. P. Pandolfi, P. G. Pellicci, and G. Parmiani. 1993. Human CD4 lymphocytes specifically recognize a peptide representing the fusion region of the hybrid protein pml/RARalpha present in acute promyelocytic leukemia cells. Blood 5:1369.

9. Kwak L. W., M. J. Campbell, B. S. Czerwinski, S. Hart, R. A. Miller, and R. Levy. 1992. Induction of immune responses in patients with B-cell lymphoma against the surface-immunoglobulin idiotype expressed by their tumors. N. Engl. J. Med. 327:1209.

10. Braciale T. J., and V. L. Braciale. 1991. Antigens presentation: structural themes and functional variations. Immunol. Today 12:124.

11. Falk K., O. Rotzschke, S. Stevanovic, G. Jung, and H. G. Rammansee. 1991. Allele-specific motifs revealed by sequencing of self-peptides eluted from MCH molecules. Nature 351:290.

12. Hoskin N. A., and M. J. Bevan. 1990. Defective presentation of endogenous antigen by a cell line expressing class I molecules. Science 248:367.

13. Stuber G., S. Modrow, P. Houglund, L. Franksson, J. Elvin, H. Wolf, K. Karre, and G. Klein. 1992. Assessment of major histocompatibility complex class I interaction with Epstein-Barr virus and human immunodeficiency virus peptides by elevation of membrane H-2 and HLA in peptide loading-deficient cells. Eur. J. Immunol. 22:2697.

14. Ruppert J., J. Sidney, E. Celis, R. T. Kubo, H. M. Grey, and A. Sette. 1993. Prominent role of secondary residues in peptide binding to HLA-A2.1 molecules. Cell 74:929.

16. Engelhard V. H. 1994. Structure of peptides associated with MHC class I molecules. Curr. Opin. Immunol. 6:13.

17. Elliott T., M. Smith, P. Driscoll, and A. McMichael. 1993. Peptide selection by class I molecules of the major histocompatibility complex. Curr. Biol. 3:854.

18. Engelhard V. H. 1994. Structure of peptides associated with class I and class II MHC molecules. Annu Rev Immunol 12:181.

19. Kubo R. T., A. Sette, H. M. Grey, E. Appella, K. Sakaguchi, N. Z. Zhu, D. Arnott. N. Sherman, J. Shabanowitz, H. Michel, W. M. Bodnar, T. A. Davis, and D. F. Hunt. 1994. Definition of specific peptide motifs for four major HLA-A alleles. J. Immunol. 152:3913.

20. Hunt D. F., R. A. Henderson, J. Shabanowitz, K. Sakaguchi, H. Michel, N. Servilir, A. L. Cox, E. Appella, and V. H Engelhard. 1992. Characterization of peptides bound to the class I molecule HLA A2.1 by mass spectrometry. Science 255:1261.

21. Jardetzky T. S., W. S. Lane, R. A. Robinson, D. R. Madden, and D. C. Wiley. 1991. Identification of self peptides bound to purified HLA B27. Nature 353:326.

22. Huczko E. L., W. M. Bodnar, D. Benjamin, K. Sakaguchi, N. Z. Zhu, J. Shabanowitz, R. A. Henderson, E. Appella, D. F. Hunt, and V. H. Engelhard. 1993. Characteristics of endogenous peptides eluted from the class I MHC molecule HLA-B7 determined by mass spectometry and computer modeling. J. Immunol. 151:2572.

23. Cullis J. O., A. J. Barret, J. M. Goldman, and R. I. Lechler. 1994. Binding of BCR/ABL junctional peptides to major histocompatibility complex (MHC) class I molecules: studies in antigen-processing defective cell lines. Leukemia 8:165.

24. Kawakami Y., S. Eliyahu, K. Sakaguchi, P. F. Robbins, L. Rivoltini, J. R. Yanelli, E. Appella, and S. A. Rosenberg. 1994. Identification of the immunodominant peptides of the MART-1 human melanoma antigen recognized by the majority of HLA-A2 restricted tumor infiltrating lymphocytes. J. Exp. Med. 180:347.

26. Celis E., V. Tsai, C. Crimi, R. DeMars, P. A. Wentworth, R. W. Chesnut, H. M. Grey, A. Sette, and M. S. Horacio. 1994. Induction of anti-tumor cytotoxic T lymphocytes in normal humans using primary cultures and synthetic peptide epitopes. Proc. Natl. Acad. Sci. USA. 91:2105.

27. Antin J. H. 1993. Graft-versus-leukemia: no longer an epiphenomenon. Blood 82:2273.

REFERENCES FOR EXAMPLES 2 AND 4

1. Rowley J D: A new consistent chromosomal abnormality in chronic myelogenous leukemia, identified by quinacrine fluorescence and Giemsa staining. Nature 243:290, 1973

2. de Klein A, Geurts van Kessel A, Grosveld G, Bartram C R, Hagemeijer A, Boostma D, Spurr N K, Heisterkamp N, Groffen J, Stephenson J R: A cellular oncogene is translocated to the Philadelphia chromosome in chronic myelocytic leukemia. Nature 300:765, 1982

3. Heisterkamp N, Stephenson J R, Groffen J, Hansen P F, de Klein A, Bartram C R, Grosveld G: Localization of the c-abl oncogene adjacent to a translocation breakpoint in chronic myelocytic leukemia Nature 306:239, 1983

4. Shtivelman E, Lifshitz B, Gale R P, Canaani E: Fused transcript of abl and bcr genes in chronic myelogenous leukemia. Nature 315:550, 1985

5. Grosveld G, Verwoerd T, van Agthoven T, de Klein A, Ramachandran K L, Heisterkamp N, Stam K, Groffen J: The chronic myelocytic cell line K562 contains a breakpoint in bcr and produces a chimeric bcr-abl chimeric transcript. Mol cell Biol 6:607, 1986

6. Ben-Neriah Y, Daley G Q, Mes-Massan A M, Wirte O N, Baltimore D: The chronic myelogenous leukemia-specific P210 protein is the product of the bcr/abl hybrid gene: Science 233:212, 1986

7. Kloetzer W, Kurzrock R, Smith L, Talpaz M, Spiller M, Gutterman J, Arlinghaus R: The human cellular abl gene product in the chronic myelogenous leukemia cell line K562 has associated tyrosine protein kinase activity. Virology 140:230, 1985

8. Shitvelman E, Lifshitz B, Gale R P, Roe B A, Canaani E: Alternative splicing of RNAs transcribed from the human abl gene and from the bcr-abl fused gene. Cell 47:277, 1986

9. van Denderen J, Hermans A, Meeuwsen T, Troelstra C, Zegers N, Boersma W, Grosveld G, van Ewijk W: Antibody recognition of the tumor specific bcr-abl joining region in chronic myeloid leukemia. J Exp Med 169:87, 1989

10. Dhut S, Chaplin T, Young B D: BCR-ABL and BCR proteins: biochemical characterization and localization. Leukemia 4:745, 1990

11. Chen W, Peace D J, Rovira D K, Sheng-guo Y, Cheever MA: T-cell immunity to the joining region of p210 bcr-abl protein. Proc Natl Acad Sci USA 89:1468, 1992

12. Gambacorti-Passerini C, Grignani F, Arienti F, Pandolfi P P, Pellicci P G, Parmiani G: Human CD4 lymphocytes specifically recognize a peptide representing the fusion region of the hybrid protein pml/RAR alpha present in acute promyelocytic leukemia cells. Blood 5:1369, 1993

13. Jung S., and H. J. Schiusener. 1991. Human T lymphocytes recognize a peptide of single point-mutated, oncogenic ras proteins. J. Exp. Med. 173:273.

14. See Example 1.

15. Kubo R. T., A. Sette, H. M. Grey, E. Appella, K. Sakaguchi, N. Z. Zhu, D. Arnott. N. Sherman, J. Shabanowitz, H. Michel, W. M. Bodnar, T. A. Davis, and D. F. Hunt. 1994. Definition of specific peptide motifs for four major HLA-A alleles. J. Immunol. 152:3913.

18. Kawakami Y., S. Eliyahu, K. Sakaguchi, P. F. Robbins, L. Rivoltini, J. R. Yanelli, E. Appella, and S. A. Rosenberg. 1994. Identification of the immunodominant peptides of the MART-1 human melanoma antigen recognized by the majority of HLA-A2 restricted tumor infiltrating lymphocytes. J. Exp. Med. 180:347.

19. Engelhard V H. Structure of peptides associated with MHC class I molecules. Curr Opin Immunol 6:13. 1994

20. Elliott T., M. Smith, P. Driscoll, and A. McMichael. 1993. Peptide selection by class I molecules of the major histocompatibility complex. Curr. Biol. 3:854.

21. Engelhard V. H. 1994. Structure of peptides associated with class I and class II MHC molecules. Annu Rev Immunol 12:181.

22. Hunt D. F., R. A. Henderson, J. Shabanowitz, K. Sakaguchi, H. Michel, N. Servilir, A. L. Cox, E. Appella, and V. H Engelhard. 1992. Characterization of peptides bound to the class I molecule HLA A2.1 by mass spectrometry. Science 255:1261.

23. Jardetzky T. S., W. S. Lane, R. A. Robinson, D. R. Madden, and D. C. Wiley. 1991. Identification of self peptides bound to purified HLA B27. Nature 353:326.

24. Kensil C R, Patel U, Lennick M, Marciani D. Separation and characterization of saponins with adjuvant activity from Quillaja saponaria Molina cortex. J Immunol 146:431. 1991.

25. Marciani D J, Kensil C R, Beltz G A, Hung C, Cronier J, Auberg A. Genetically engineered subunit vaccine against feline leukemia virus: Protective immune response in cats. Vaccine 9:89. 1991.

26. Newman M J, Munroe K J, Anderson C A, Murpha C I, Panicali D L, Seals J R, Wu J-Y, Wyand M S, Kensil C R. Induction of antigen-specific killer T lymphocyte responses using subunit $SIV_{mac251}$ gag and env vaccines containing QS-21 saponin adjuvant. Aids Research and Human Retroviruses 10:853. 1994

27. Livingston P O, Adluri S, Helling F, Yao T-J, Kensil C R, Newman M J, Marciani D. Phase 1 trial of immunological adjuvant QS-21 with a GM2 ganglioside-keyhole limpet haemocyanin conjugate vaccine in patients with malignant melanoma. Vaccine 12:14. 1994.

---

What is claimed is:

1. A method of inducing formation and proliferation of human cytotoxic T cells from human peripheral blood mononuclear cells (PBMCs) comprising contacting human peripheral blood mononuclear cells with a peptide consisting of amino acids, the amino acid sequence of which is selected from the group consisting of: the following: 1) ATGFKQSSK (SEQ ID NO:28); 2) KQSSKALQR (SEQ ID NO:32); 3) HSATGFKQSSK (SEQ ID NO:2); 4) GFKQSSKAL (SEQ ID NO:30); and 5) IVHSATGFKQSSKALORPVASDFEP (SEO ID NO:34) so as to thereby induce formation and proliferation of human cytotoxic T cells.

2. The method of claim 1, wherein the human peripheral blood mononuclear cells are CD8+ cells.

3. The method of claim 1, wherein the human peripheral blood mononuclear cells are CD4+ cells.

4. The method of claim 1, wherein the human cytotoxic T cells and human peripheral blood mononuclear cells are present in a subject and the contacting is effected by administering the peptide to the subject.

5. A composition which comprises a peptide which consists of amino acids, the amino acid sequence of which is selected from the group consisting of the following: 1) ATGFKQSSK (SEQ ID NO:28); 2) KQSSKALQR (SEQ ID NO:32); 3) HSATGFKQSSK (SEQ ID NO:2); 4) GFKQSSKAL (SEQ ID NO:30); and 5)IVHSATGFKQSSKALQRPVASDFEP (SEQ ID NO:34).

6. A composition which comprises a carrier and a therapeutically effective amount of a peptide which consists of amino acids, the amino acid sequence of which is selected from the group consisting of the following: 1) ATGFKQSSK (SEQ ID NO:28); 2) KQSSKALQR (SEQ ID NO:32); 3) HSATGFKQSSK (SEQ ID NO:2); 4) GFKQSSKAL (SEQ ID NO:30); and 5)IVHSATGFKQSSKALQRPVASDFEP (SEQ ID NO:34) the composition being effective for inducing formation and proliferation of human cytotoxic T cells from human peripheral blood mononuclear cells (PBMCs) in a subject.

7. The composition of claim 6, wherein the human peripheral blood mononuclear cells are CD8+ cells.

8. The composition of claim 6, wherein the human peripheral blood mononuclear cells are CD4+ cells.

* * * * *

UNITED STATES PATENT AND TRADEMARK OFFICE
CERTIFICATE OF CORRECTION

PATENT NO. : 6,156,316 Page 1 of 1
DATED : December 5, 2000
INVENTOR(S) : Scheinberg, David A.

It is certified that error appears in the above-identified patent and that said Letters Patent is hereby corrected as shown below:

<u>Column 35,</u>
Lines 42-43, should read -- GFKQSSKAL (SEQ ID NO:30); and 5) IVHSATGFKQSSKALQRPVASDFEP (SEQ ID NO:34) so as to thereby --.

Signed and Sealed this

Seventh Day of February, 2006

JON W. DUDAS
*Director of the United States Patent and Trademark Office*